United States Patent [19]

Lee et al.

[11] Patent Number: 5,162,534
[45] Date of Patent: Nov. 10, 1992

[54] PROCESS FOR THE PREPARATION OF THIAZOLINE DERIVATIVES

[75] Inventors: Kee-Jung Lee; Dae O. Choi; Jae U. Jeong; Ho K. Park, all of Seoul, Rep. of Korea

[73] Assignee: Korea Institute of Science and Technology, Seoul, Rep. of Korea

[21] Appl. No.: 723,253

[22] Filed: Jun. 28, 1991

Related U.S. Application Data

[62] Division of Ser. No. 634,001, Dec. 26, 1990, abandoned.

[30] Foreign Application Priority Data

Jul. 14, 1990 [KR] Rep. of Korea ............... 10721/1990

[51] Int. Cl.⁵ .................. C07D 409/00; C07D 277/04
[52] U.S. Cl. ..................................... 546/280; 548/183
[58] Field of Search .......................... 548/183; 546/280

[56] References Cited

PUBLICATIONS

Maeda, et al., Chem. Pharm. Bull., 31(10) 3424 and 3432 (1983).
Japanese Patent Laid-Open No. 60-184,070 (1985).
J. Org. Chem., 30, 491, 1965.
J. Org. Chem., 36, 1068, 1971.

Primary Examiner—Mary C. Lee
Assistant Examiner—Robert C. Whittenbaugh
Attorney, Agent, or Firm—Birch, Stewart, Kolasch & Birch

[57] ABSTRACT

A process for the preparation of 5-alkoxy-2-substituted thio-1,3-thiazoline derivatives of general formula (I) which can be used as herbicide, fungicide or insecticide and as useful intermediates in preparing their derivatives.

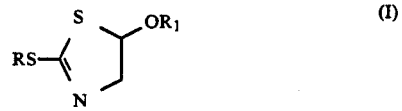

wherein, R is hydrogen, $C_1$–$C_6$ alkyl, allyl, 2-propynyl, benzyl, and 2-pyridylmethyl and $R_1$ is methyl and ethyl.

3 Claims, No Drawings

PROCESS FOR THE PREPARATION OF THIAZOLINE DERIVATIVES

This application is a divisional of application Ser. No. 534,001, filed on Dec. 26, 1990, now abandoned. The entire contents of which are hereby incorporated by reference.

BACKGROUND OF THE INVENTION

The present invention relates to a process for the preparation of novel 5-alkoxy-2-substituted thio-1,3-thiazoline derivatives of general formula(I) (hereinafter, referred to a ("thiazoline derivatives"). More specifically, thiazoline derivatives of general formula(I) of the present invention can be used as herbicide, fungicide or insecticide and as useful intermediates in preparing their derivatives. (Japan Patent No. 85-184,070)

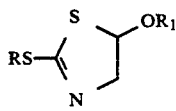
(I)

Wherein, R is hydrogen, $C_1$-$C_6$ alkyl, allyl, 2-propynyl, benzyl, and 2-pyridylmethyl and $R_1$ is methyl and ethyl.

The thiazoline derivative of general formula(I) according to the present invention is a novel compound which is not disclosed in any literatures. However, the process for preparing thiazoline derivatives of general formula(II) similar to that of this invention is disclosed in scientific magazines (J. Org. Chem., 1965, 30, 491 and J. Org. Chem, 1971, 36, 1068) as follows:

2-aminoethyl sulfate of general formula(III) or aziridine derivatives of general formula(IV) is reacted with ethylxanthic acid, potassium salt ($EtOCS_2K$) or carbon disulfide respectively to prepare thiazolidine-2-thione of general formula(V). Then, the resulting material is reacted with alkylating agent in the presence of a base to prepare thiazoline derivatives of general formula(II)

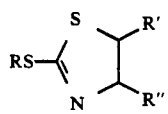
(II)

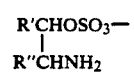
(III)

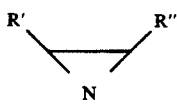
(IV)

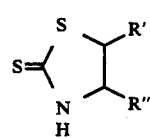
(V)

Wherein, R is methyl; R' and R" are hydrogen, alkyl or phenyl group.

The inventors attempted to research on the basis of the above-mentioned known process technique in order to prepare thiazoline derivatives of general formula(I) (R is hydrogen) available as useful intermediates of cephalosporin derivatives. That is, in order to prepare thiazoline derivatives of general formula(I), the inventors tried to prepare the compound of general formula (III) or (IV) (R' or R" is alkoxy group) but could not succeed.

The present inventors found that there were many problems in preparing thiazoline derivatives of general formula(I) by the known process and studied continuously to reach a new method. Thus, according to the present invention, dithiocarbamate of general formula (VI) is readily converted into thiazoline derivatives of general formula(I) by intramolecular cyclization.

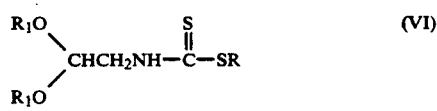
(VI)

Wherein, R and R' are defined as the above general formula (I).

SUMMARY OF THE INVENTION

Accordingly, it is an object of the invention to provide a process for preparing thiazoline derivatives of general formula(I). More specifically, dithiocarbamate of general formula(VI) may be used by intramolecular thermal rearrangement under reduced pressure (approximately, 1 to 5 mmHg) at 200°±10° C. and also the intramolecular cyclization may be occurred in the presence of a acid to obtain the desired thiazoline derivatives of general formula(I) as a high yield.

Acids which can be used in preparing thiazoline derivatives of general formula(I) include trifluoroborane, anhydrous magnesium bromide or concentrated sulfuric acid, and most preferably trifluoroborane. The suitable solvent in the said reaction is dichloromethane, dichloroethane, chloroform or carbon tetrachloride and the reaction temperature is preferably 10°±5° C.

Another object of the present invention is to provide process which can obtain novel compounds, thiazoline derivatives of general formula(I) from dithiocarbamate of general formula(VI), readily available raw material as a high yield (more than 95%).

Dithiocarbamate of general formula(VI) can be readily prepared as described in Scientific Journal (Synthesis, 1989, 638); aminoacetal of general formula(VII) is reacted with carbon disulfide in the presence of triethylamine at 0° to 20° C. for one hour to obtain a compound of general formula(VIII). To the resulting compound is added concentrated hydrochloric acid or alkyl halide, and reacted at the same temperature for 1 to 2 hours.

DETAILED DESCRIPTION OF THE INVENTION

To further the understanding of this invention, a process for the preparation of the final material from the starting material is expressed in the following scheme.

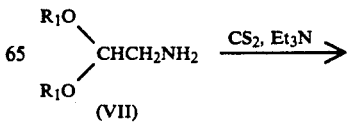
(VII)

$$\begin{array}{c} R_1O \\ \phantom{R_1O} \diagdown \\ \phantom{R_1O} \phantom{\diagdown} CHCH_2NH-\overset{S}{\underset{\|}{C}}-S^-Et_3\overset{+}{N}H \\ \phantom{R_1O} \diagup \\ R_1O \end{array} \xrightarrow{RX}$$

(VIII)

$$\begin{array}{c} R_1O \\ \phantom{R_1O} \diagdown \\ \phantom{R_1O} \phantom{\diagdown} CHCH_2NH-\overset{S}{\underset{\|}{C}}-SR \\ \phantom{R_1O} \diagup \\ R_1O \end{array} \xrightarrow{\text{distillation or acid}}$$

(VI)

$$\underset{N}{\underset{\diagup}{R_1O}}\overset{S}{\diagdown}\!\!\!\!\!\!\!\diagup\!\!\text{-SR}$$

(I)

Wherein, $R_1$ is defined as the above general formula(I). The present following examples are intended to illustrate the invention in further detail, as non-limiting examples. However, it will be appreciated that modification and variation can be made by those skilled in the art without departing from the spirit and scope of the present invention.

EXAMPLE 1

Preparation of methyl N-(2,2-dimethoxyethyl)dithiocarbamate (VI, R=$R_1$=methyl)

To a solution of 21 g (0.2 mole) of aminoacetaldehyde dimethylacetal in 150 ml of ethanol and 10 ml of water was added 24.3 g (0.24 mole) of triethylamine, and 16.8 g (0.22 mole) of carbon disulfide in portions at 0° to 5° C. After the reaction mixture was stirred for one hour at the same temperature, 31.2 g (0.22 mole) of methyl iodide was added dropwise in portions, and then was further stirred for one hour at 15°±5° C. The solvent was removed under reduced pressure (30 mmHg) and water was added thereto. Then, the mixture was extracted with ethylacetate, dried over anhydrous sodium sulfate and filtered. The solvent was removed under reduced pressure (30 mmHg) to obtain the desired liquid compound, 36.9 g (yield 95%).

$^1$H-NMR δ (CDCl$_3$) : 2.32(s,3H), 3.11(s,6H), 3.57(t,J=5.1, 2H), 4.28(t,J=5.1,1H), 7.50(br s, 1H)

EXAMPLE 2

Preparation of methyl N-(2,2-diethoxyethyl)dithiocarbamate (VI, R=methyl, $R_1$=ethyl)

To a solution of 4 g (0.03 mole) of aminoacetaldehyde diethylacetal in 60 l of tetrahydrofuran was added 3.3 g (0.033 mole) of triethylamine and 2.5 g (0.033 mole) of carbon disulfide. After the reaction mixture was stirred for one hour at 0° to 5° C., 4.7 g (0.033 mole) of methyl iodide was slowly added and stirred at 15°±5° C. for one hour. The solvent was removed from the reactant under reduced pressure, and water was added. The resulting mixture was extracted with ethyl acetate, dried over anhydrous sodium sulfate, and filtered. The solvent was removed under reduced pressure to obtain 6.54 g (yield 98%) of the desired liquid compound.

$^1$H-NMR δ (CDCl$_3$): 1.23(t,J=7.0, 6H), 2.63(s,3H), 3.41-4.04 (m,6H), 4.70(t,J=5.0,1H), 7.31(br s, 1H)

EXAMPLE 3

Preparation of ethyl N-(2,2-dimethoxyethyl)dithiocarbamate (VI, R=ethyl, $R_1$=methyl)

Using the same procedure as that described in Example 1, 10.5 g (0.1 mole) of aminoacetaldehyde dimethylacetal was reacted with 12 g (0.11 mole) of ethyl bromide for 2 hours to obtain 19.9 g (yield 95%) of the desired liquid compound.

$^1$H-NMR δ (CDCl ) : 1.33(t,J=7.5,3H), 3.27(q,J=7.5,2H), 3.43(s,6H), 3.87(t,J=5.0,2H), 4.57(t, J=5.0,1H), 7.43(br s, 1H)

EXAMPLE 4

Preparation of allyl N-(2,2-dimethoxyethyl)dithiocarbamate(VI, R=allyl, $R_1$=methyl)

Using the same procedure as that described in Example 1, 10.5 g (0.1 mole) of aminoacetaldehyde dimethylacetal was reacted with 13.3 g (0.11 mole) of allyl bromide for 30 minutes to obtain 21.2 g (yield 96%) of the desired liquid compound.

$^1$H-NMR δ (CDCl$_3$) : 3.43(s,6H), 3.80-4.03(m,4H), 4.60(t, J=5.0,1H), 5.07-5.53(m,2H), 5.67-6.23 (m,1H), 7.43(br s,1H)

EXAMPLE 5

Preparation of 2-propynyl N-(2,2-diemthoxyethyl)dithiocarbamate (VI, R=2-propynyl, $R_1$=methyl)

10.5 g (0.1 mole) of aminoacetaldehyde dimethylacetal was dissolved in 100 ml of tetrahydrofuran and 12.2 g (0.12 moles) of triethylamine and 8.4 g (0.11 mole) of carbon disulfide were added. After the mixture was stirred at 0° to 5° C. for one hour and cooled to −78° C., 13.1 g (0.11 mole) of 2-propynyl bromide was added dropwise in portions. After 10 minutes, the precipitated amine salts was removed by filtration and the filtrate was concentrated under reduced pressure (30 mmHg) to obtain 21.1 g (yield 92%) of the desired liquid compound.

$^1$H-NMR δ (CDCl$_3$) : 2.29(t,J=2.5,1H), 3.47(s,6H, 3.89(t, J=5.7,2H), 4.09 (d,J=2.5,2H), 4.87(t, J=5.5,1H), 7.42(br s, 1H)

EXAMPLE 6

Preparation of benzyl N-(2,2-dimethoxyethyl)dithiocarbamate (VI, R=benzyl, $R_1$=methyl)

Using the same procedure as that described in Example 1, 10.5 g (0.1 mole) of aminoacetaldehyde dimethylacetal was reacted with 13.9 g (0.11 mole) of benzyl chloride to obtain 26.3 g (yield 97%) of the desired liquid compound.

$^1$H-NMR δ (CDCl$_3$) : 3.40(s,6H), 3.90(t,J=5.1, 2H), 4.53-4.63 (m,3H), 7.23-7.53(m6H)

EXAMPLE 7

Preparation of 2-pyridylmethyl N-(2,2-dimethoxyethyl)dithiocarba mate (VI, R=2-pyridylmethyl, $R_1$=methyl)

Using the same procedure as that described in Example 1, 10.5 g (0.1 mole) of aminoacetaldehyde dimethylacetal was reacted with 18.0 g (0.11 mole) of 2-chloromethylpyridine hydrochloride to obtain 25.8 g (yield 95% of the desired solid compound melting point: 51° C.

$^1$H-NMR δ (CDCl$_3$) : 3.44(s,6H), 3.93(t,J=5.5, 2H), 4.30(s, 2H), 5.68(t,J=5.5,1H), 7.13-8.63(m,4H), 10.83(br s,1H)

EXAMPLE 8

Preparation of N-(2,2-dimethoxyethyl)dithiocarbamate(VI, R=hydrogen, R₁=methyl)

10.5 g (0.1 moles) of aminoacetaldehyde dimethylacetal was dissolved in 100 ml of tetrahydrofuran and 11.1 g (0.11 moles) of triethylamine, 7.6 g (0.11 moles) of carbon disulfide were added, and the mixture was stirred at 0° to 5° C. for one hour. To the reaction mixture was added concentrated hydrochloric acid (9 ml). Then, the mixture was dried over anhydrous sodium sulfate and filtered. The filtrate was removed under reduced pressure (30 mmHg) to obtain 13.0 g (yield 72%) of the desired liquid compound.

$^1$H-NMR δ (CDCl$_3$) : 3.41(s,6H), 3.57(d,J=5.2,2H), 4.47(t, J=5.0,1H), 6.79(br s,1H)

EXAMPLE 9

Preparation of 5-methoxy-2-methylthio-1,3-thiazoline (I, R=R$_1$=methyl)

1) Method using heat transfer 19.5 g (0.1 mole) of dithiocarbamate (VI) obtained from the method of Example 1 was slowly distilled under reduced pressure (1 to 5 mmHg) at 200°±10° C. to obtain 12.2 g (yield 75%) of the desired thiazoline compound.

$^1$H-NMR δ (CDCl$_3$) : 2.53(s,3H), 3.26(s,3H), 4.04(dd,J=16.2, 5.62,1H), 4.45(d,J=16.2,1H), 5.62(d,J=5.62,1H)

2) Method using BF$_3$

After 4.88 g (0.025 mole) of dithiocarbamate (VI) obtained from the method of Example 1 was dissolved in 50 ml of dichloromethane, 3.9 g (0.0275 mole) of trifluoroborane ether was added dropwise in small portions at 10°±5° C. and stirred at the same temperature for 10 minutes. The reaction mixture was adjusted to pH8-9 by neutralizing with saturated aqueous solution of sodium hydrogen carbonate and then extracted with dichloromethane (50 ml×2). After drying over anhydrous sodium sulfate, the solvent was removed under reduced pressure (30 mmHg) to obtain 3.0 g (yield 98%) of the desirable thiazoline.

3) Method using MgBr$_2$

After 4.88 g (0.025 mole) of dithiocarbamate (VI) obtained from the method of Example 1 was dissolved in 50 ml of dichloromethane, 7.1 g (0.0275 mole) of anhydrous magnesium bromide was added at 10°±5° C. and stirred at the same temperature for 20 minutes. The resulting mixture was treated as the method of Example 9-2) to obtain 4.0 g (yield 98%) of the desired thiazoline compound.

4) Method using H$_2$SO$_4$

After 4.88 g (0.025 mole) of dithiocarbamate (VI) obtained from the method of Example 1 was dissolved in 50 ml of carbon tetrachloride, 2.58 g (0.025 mole) of 95% concentrated sulfuric acid was added and remained under reflux for three hours. The solid precipitation formed by cooling the reaction mixture to about 5° C. was filtered and the solid was dissolve din water. The said aqueous solution was neutralized with 5% aqueous solution of sodium hydroxide and then extracted with dichloromethane (50 ml×2). The extrate was dried over anhydrous sodium sulfate and removed the solvent under reduced pressure (30 mmHg) to obtain 3.1 g (yield 76%) of the desired thiazoline compound.

EXAMPLE 10

Preparation of 5-methoxy-2-ethylthio-1,3-thiazoline (I,R=ethyl, R$_1$=methyl)

1) Method using heat transfer 20.9 g (0.1 mole) of dithiocarbamate(VI) obtained from the method of Example 3 was slowly distilled under reduced pressure (1 to 5 mmHg) at 200°±10° C. to obtain 12.4 g (yield 70%) of the desired thiazoline compound.

$^1$H-NMR (CDCl$_3$) : 1.35(t,J=7.4,3H), 3.10(qd,J=7.4, 3.2, 2H), 3.25(s,3H), 4.08(dd,J=16.1, 5.5,1H), 4.43(d,J=16.1,1H), 5.60(d, J=5.4,1H)

2) Method using BF$_3$ 5.23 g (0.025 mole) of dithiocarbamate (VI) obtained from the Method of Example 3 was reacted using the same procedure as that in Example 9-2 to obtain 4.25 g (yield 96%) of the desired thiazoline compound.

EXAMPLE 11

Preparation of 5-methoxy-2-allylthio-1,3-thiazoline(I,R=allyl, R$_1$'methyl)

1) Method using heat transfer 22.1 g (0.1 mole) of dithiocarbamate(VI) obtained from Example 4 was slowly distilled under reduced pressure (1 to 5 mmHg) at 200°±10° C. to obtain 11.7 g (yield 62%) of the desired thiazoline compound.

$^1$H-NMR δ (CDCl$_3$) : 3.27(s,3H), 3.75–3.81(m,2H), 4.11 (dd,J=16.2,5.6,1H), 4.47(d,J=16.2, 1H). 5.14(d,J=8.7,1H), 5.28(d,J=17.1,1H), 5.62(d,J=5.6,1H), 5.84–6.00(m,1H)

2) Method using BF$_3$ 5.53 g (0.025 mole) of dithiocarbamate(VI) obtained from Example 4 was reacted using the same procedure as that in Example 9-2 to obtain 4.68 g (yield 99%) of the desired thiazoline compound.

EXAMPLE 12

Preparation of 5-methoxy-2-(2-propynylthio)-1,3-thiazoline (I, R=2-propynyl, R$_1$=methyl)

5.48 g (0.025 mole) of dithiocarbamate obtained from Example 5 was reacted by the same procedure as that in Example 9-2 to obtain 4.58 g (yield 98%) of the desired thiazoline compound.

$^1$H-NMR (CDCl$_3$) : 2.27(t,J=2.6,1H), 3.27(s,3H), 3.89(dd, J=9.4,2.6,2H), 4.11(dd,J=16.3,5.5,1H), 4.48(d,J=16.3,1H), 5.67(d,J=5.4,1H)

EXAMPLE 13

Preparation of 5-methoxy-2-benzylthio-1,3-thiazoline (I, R=benzyl, R$_1$=methyl)

6.78 g (0.025 mole) of dithiocarbamate obtained from Example 6 was reacted by the same procedure as that in Example 9-2 to obtain 5.80 g (yield 97%) of the desired thiazoline compound.

$^1$H-NMR δ (CDCl$_3$) : 3.20(s,3H), 4.05(dd,J=16.2,5.4,1H), 4.30(d,J=13.0,1H), 4.39(d,J=13.0,1H), 4.45(d,J=16.2,1H), 5.54(d,J=5.4,1H), 7.20–7.25(m,5H)

EXAMPLE 14

Preparation of 5-methoxy-2-pyridylmethylthio-1,3-thiazoline (I, R=2-pyridylmethyl, $R_1$=methyl)

68.1 g (0.025 mole) of dithiocarbamate (VI) obtained from Example 7 was reacted with 8.51 g (0.06 mole) of trifluoroborane ether according to the same procedure as that in Example 9-2 to obtain 5.82 g (yield 97%) of the desired thiazoline compound.

$^1$H-NMR δ (CDCl$_3$) : 3.38(s,3H), 4.23(dd,J=16.2,5.5,1H), 4.60 (d,J=16.2,1H), 4.64(d,J=4.6,2H), 5.75 (d,J=8.5,1H), 7.25–7.78(m,3H), 8.64–8.67 (m,1H)

EXAMPLE 15

Preparation of 5-methoxy-2-thio-1,3-thiazoline(I,R=hydrogen $R_1$=methyl)

4.53 g (0.025 mole) of dithiocarbamate (VI) obtained from Example 8 was reacted by the same procedure as that in Example 9-2 to obtain the solid compound. This was recrystallized from ether to obtain 2.76 g (yield 74%) of the desired thiazoline compound.

melting point: 77° C.

$^1$H-NMR δ (CDCl$_3$) : 3.40(s,3H), 4.05(dd,J=14.0,0.9,1H), 4.19 (dd,J=13.0,5.2,1H), 5.54(dd,J=5.0,0.9, 1H), 8.79(br s,1H)

EXAMPLE 16

Preparation of 5-ethoxy-2-methylthio-1,3-thiazoline (I,R=methyl, $R_1$=ethyl)

5.58 g (0.025 mole) of dithiocarbamate (VI) obtained from Example 2 was reacted by the same procedure as that in Example 9-2 to obtain 4.21 g (yield 95%) of the desired thiazoline compound.

$^1$H-NMR δ (CDCl$_3$) : 1.20(t,J=7.0,3H), 2.54(s,3H), 3.39 and 3.56(two dq, J=7.0,5.0,2H), 4.10(dd, J=16.0,5.5,1H), 4.46(dd,J=16.1,0.5,1H), 5.70(dd,J=5.5,0.5,1H)

What is claimed is:

1. A process of preparing thiazoline derivatives of the following formula (I), which comprises interamolecularly cyclizing dithiocarbamate of the following formula (IV) under thermal rearrangement and in the presence of acid

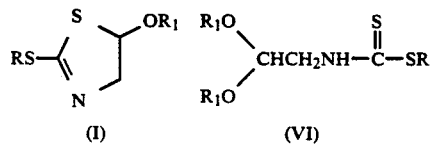

wherein, R is hydrogen, $C_1$–$C_6$ alkyl, allyl, 2-propynyl, benzyl and 2-pyridylmethyl; and $R_1$ is methyl or ethyl.

2. The process of claim 1, wherein the thermal rearrangement is carried out at a temperature of 200°±10° C. under reduced pressure of 1 to 5 mmHg.

3. The process of claim 1, wherein the acid is selected from a group consisting of trifluoroborane, anhydrous magnesium bromide, and concentrated sulfuric acid.

* * * * *